United States Patent [19]

Weil

[11] 4,067,927

[45] Jan. 10, 1978

[54] COPOLYCONDENSED VINYLPHOSPHONATES AND THEIR USE AS FLAME RETARDANTS

[75] Inventor: Edward D. Weil, Hastings-on-Hudson, N.Y.

[73] Assignee: Stauffer Chemical Company, Westport, Conn.

[21] Appl. No.: 701,332

[22] Filed: June 30, 1976

Related U.S. Application Data

[60] Continuation of Ser. No. 505,122, Sept. 11, 1974, abandoned, which is a division of Ser. No. 187,575, Oct. 7, 1971, Pat. No. 3,855,359, which is a continuation-in-part of Ser. No. 153,075, June 14, 1971, Pat. No. 3,822,327.

[51] Int. Cl.$^2$ .................. C08L 63/00; C08L 67/06; C08F 14/02
[52] U.S. Cl. .................... 260/836; 260/2 P; 260/17 A; 260/17 R; 260/47 UA; 260/47 UP; 260/63 UY; 260/837 R; 260/862; 260/873; 260/DIG. 24; 526/11.1; 526/17; 526/46; 526/55; 526/278

[58] Field of Search .................. 260/2 P, 17 A, 17 R, 260/63 UY, 873, DIG. 24, 836, 837 R, 862, 47 UP, 47 UA; 526/17, 55, 46, 278, 11.1

[56] References Cited

U.S. PATENT DOCUMENTS

| 3,558,596 | 1/1971 | Demott | 260/218 |
|---|---|---|---|
| 3,854,989 | 12/1974 | Colborn | 260/DIG. 24 |
| 3,878,245 | 4/1975 | Nachbur et al. | 260/2 P |

FOREIGN PATENT DOCUMENTS

| 1,243,192 | 6/1967 | Germany | 260/928 |
|---|---|---|---|
| 148,057 | 12/1962 | U.S.S.R. | 260/928 |
| 202,126 | 11/1967 | U.S.S.R. | 260/928 |

OTHER PUBLICATIONS

Chem. Abs., vol. 66, 1967, # 86180f Yuldasher et al.

*Primary Examiner*—Herbert J. Lilling
*Attorney, Agent, or Firm*—William R. Robinson

[57] ABSTRACT

There are disclosed novel copolycondensed vinylphosphonates and a process for their preparation. These products may be used as flame retardant monomers and are especially suitable for flame retarding textiles and a variety of other flammable substrates.

11 Claims, No Drawings

COPOLYCONDENSED VINYLPHOSPHONATES AND THEIR USE AS FLAME RETARDANTS

RELATED APPLICATION

This is a continuation of application Ser. No. 505,122 filed Sept. 11, 1974, and now abandoned, which in turn was a division of application Ser. No. 187,575, filed Oct. 7, 1971 now U.S. Pat. No. 3,855,359, which is a continuation-in-part of copending application Ser. No. 153,075, filed June 14, 1971, now U.S. Pat. No. 3,822,327.

BACKGROUND OF THE INVENTION

The above noted copending application discloses the preparation of homopolycondensed vinylphosphonates, the neutralization of the resulting homopolycondensates with epoxide reagents and the use of these neutralized homopolycondensates for preparing flame retardant textile finishes.

TECHNICAL DISCLOSURE OF THE INVENTION

The present invention relates to the copolycondensed vinylphosphonates which are prepared by the co-condensation of: (1) a (2-haloalkyl) vinylphosphonate, or an alpha-methylvinylphosphonate, preferably (2-chloroethyl) vinylphosphonate, and/or its halohalide adduct precursor which may be, for example, a 2-haloethyl or 2-haloisopropylphosphonate, with: (2) at least one pentavalent phosphorus ester of the structure ROP(=O)XY where R is selected from the class consisting of $C_1$-$C_{20}$ alkyl, $C_1$-$C_{20}$ alkenyl and $C_1$-$C_{20}$ haloalkyl, e.g. chloro- or bromoalkyl, groups and is, preferably, a methyl, ethyl, 2-chloroethyl or beta-chloropropyl group and X and Y are groups selected from the class consisting of RO—, $C_1$-$C_{20}$ alkyl, $C_1$-$C_{20}$ alkenyl, aryl, aryloxy, amino, $C_1$-$C_{20}$ alkyl- or aryl-substituted amino groups and $C_2$-$C_{20}$ alkylene, $C_2$-$C_{20}$ alkyleneoxy, i.e. (alkylene-O-), or $C_2$-$C_{20}$ alkylenedioxy, i.e. (-O-alkylene-O-), groups bonded to the same or to another ROP(=O) moiety. Preferred groups for X and Y are methoxy, ethoxy, 2-chloroethoxy, beta-chloropropoxy (including n- and iso-), methyl and ethyl because of their ready availability, flame retardancy efficacy and rapid reaction rate. Any of the above listed groups can be further substituted with non-interfering substituents, i.e. with substituents which do not interfere with the reaction, such for example as alkoxy, cyano, carbalkoxy and carbamide groups. For particular purposes, groups other than the indicated preferred groups may be selected. For example, larger alkyl groups, up to about $C_{20}$, may be used to provide water repellency while nitrogenous groups, such as cyanoethyl or dimethylamino, may be used in the role of X and/or Y to enhance flame retardant efficacy.

The novel copolycondensed vinylphosphonates resulting from the process of this invention possess excellent flame retarding properties. They may, therefore, be used as monomers for the preparation of flame retardant resins or, if so desired, they can be used to prepare flame retardant finishes for many different types of flammable substrates such as unsaturated polyesters and particularly for textiles. Thus, these copolycondensates yield fire retardant, resinous textile finishes which are characterized by their outstanding degree of resistance to laundering and dry cleaning which is achieved without any adverse effects upon the softness, hand or other desirable physical properties of the thus treated textiles.

These novel copolycondensed vinylphosphonates display many advantages over the homopolycondensed vinylphosphonates of the prior art such as those described, for example, in the above noted copending application as well as by Yuldashev et al., Dokl. Akad. Nauk Uzbek. SSR 1968 30. Thus, when used as textile finishing agents, these copolycondensates yield finishes characterized by their superior fire retardancy and improved hand. The latter highly desirable advantage is believed to result from the more distant spacing between the crosslinking vinyl groups which are present on the polymer chains of the resulting textile finish. This apparently leads to greater flexibility on the part of the polymer. It is to be stressed, however, that the preceding explanation is only theoretical and applicant does not wish to be limited thereby. Moreover, the increased fire retardancy derived from these novel compounds is a surprising and unexpected result for which no explanation is evident.

In greater detail, now, the process of this invention is carried out by reacting a (2-haloalkyl) vinylphosphonate such as 2-bromo-, 2-fluoro or, most preferably, (2-chloroethyl) vinylphosphonate, and at least one of the above described pentavalent phosphorus esters, with the use of dimethyl methylphosphonate being preferred. Other suitable pentavalent phosphorus esters include trimethyl phosphate, triethyl phosphate, tris(2-chloroethyl) phosphate, tris(2,3-dibromopropyl) phosphate, tris($\beta$-chloropropyl) phosphate, (n- and/or isopropyl), dimethyl n-eicosyl phosphate, dimethyl phenyl phosphate, methyl allyl phosphates, dimethyl trichlorophenyl phosphate, methyl diphenyl phosphate, dimethyl phenylphosphonate, diethyl polybromobiphenylylphosphonate, methyl diphenylphosphinate, dimethyl 2,3-dibromopropyl phosphate, dimethyl N,N-dimethylphosphoramidate, methyl ethylene phosphate, ethylenebis(dimethyl phosphate), dipropylene glycol bis(di-2-chloroethyl phosphate), dichloroneopentylene bis(di-2-chloroethyl phosphate), tris(methoxyethyl) phosphate, dimethyl cyanoethylphosphonate, polycondensed 2-chloroethyl phosphates such as those disclosed in U.S. Pat. No. 3,513,644 and 2-chloroethyl phosphonate oligomers such as those disclosed in U.S. Pat. No. 3,014,956.

This reaction is conducted at an elevated temperature and for a period of time which is sufficient to evolve R-halide as a by-product and to form a P(O)-O-alkylene-O-P(O)XY linkage. The reaction will, therefore, usually require heating in the range of from about 100° to 280° C., preferably 120° to 250° C., applied over a period of from about 0.1 to 100 hours. The R-halide, such as methyl chloride, 1,2-dichloroethane, etc., by-product is usually removed by means of distillation. The reaction may be terminated when the amount of R-halide which has been liberated corresponds to the desired degree of condensation, i.e. the number of newly formed P(O)-O-alkylene-O-P(O) units, in the average polycondensate molecule.

The rate of this co-condensation reaction is improved by conducting it in the presence of an effective catalytic amount, e.g. from about 0.01 to 5%, as based on the weight of the vinylphosphonate, of a nucleophilic compound which may be a carbonate, bicarbonate or hydroxide of an alkali or alkaline earth metal such, for example, as sodium, potassium or lithium carbonate, sodium bicarbonate and calcium hydroxide or any nucleophilic reagent capable of cleaving the phosphonate ester linkage so as to generate a phosphonate anion. Other effective nucleophilic reagents for use as catalysts in this reaction include amines, alkali halides, alkali phosphates, phosphines, quaternary ammonium bases or salts and quaternary phosphonium salts. A polymerization inhibitor such, for example, as hydroquinone or other phenols, may also be optionally present in the system in a concentration of from about 0.1 ppm to 0.1%, as based on the weight of the vinyl-phosphonate in order to suppress vinyl-type, i.e. addition, polymerization during the preparation and/or the storage of the resulting copolycondensate.

With respect to proportions, the process of this invention may be conducted under conditions where the stoichiometric ratio of the (2-haloethyl) vinylphosphonate to the pentavalent phosphorus ester may be varied from about 1:10 to 10:1 with the use of a ratio of from about 1:5 to 5:1 being preferred. By appropriate choice of the reactant ROP(O)XY, adjusting the stoichiometric ratio and the degree of completion of the R-halide evolving reaction, copolycondensation products may be made ranging from monovinylphosphonates to high molecular weight linear or branched vinylphosphonate polymers. By use of 1 or 2 moles of ROP(O)XY per mole of bis(2-haloalkyl) vinylphosphonate and by limiting the reaction to the evolution of 1 or 3 moles of R-halide, monovinylphosphonates of the structure CH$_2$=CHP(O)—(OCH$_2$CH$_2$X)(OCH$_2$CH$_2$OP(O)XY) and CH$_2$=CHP(O) (OCH$_2$CH$_2$OP(O)XY)$_2$ may be made. The latter products are synthesized in optimum yield by the use of an excess of ROP(O)XY or by use of an ROP(O)XY reagent where neither X nor Y is alkoxy. Where at least one of the groups X or Y is alkoxy, polymers of the type (—OCH$_2$CH$_2$OP(O)(CH=CH$_2$) OCH$_2$CH$_2$OP(O)X—)$_x$, where $x$ can range up to 100 or higher, can be prepared. Where both X and Y are alkoxy, the condensation products can have branched molecules the point of branching being the phosphorus atom derived from the ROP(O)XY reactant. The initial products of the copolycondensation reaction of this invention can be used, as such, as monomers and as polymer-forming reactants.

Typical examples of the copolycondensation reaction of this invention include the following. The indicated structures are those of average or typical products and in most cases the reaction products are mixtures as is commonly the case in oligomerization and polymerization. Furthermore, the indicated structures illustrate only the main product structures neglecting the acidic structures which are also known to be present in minor amounts; these additional structures will be discussed in more detail hereinafter.

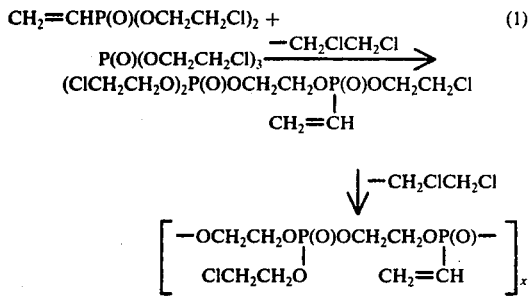

where $x$ can have a value of from about 2 to about 20. The chains are terminated by 2-chloroethoxy phosphate or phosphonate groups. Since the tris(2-chloroethyl) phosphate can react as a trifunctional reagent, branched structures related to the above are also believed to be formed.

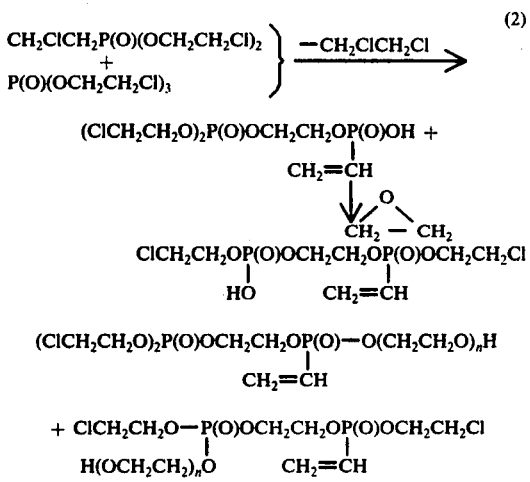

where n ≧ 1

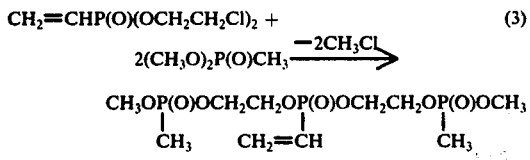

By employing reactant quantities corresponding to the above stoichiometry, the actual product obtained contains higher oligomers besides the product indicated by the formula. By employing an excess of dimethyl methylphosphonate, and subsequently distilling off the excess, a residual product highly predominent in the indicated product compound may be obtained.

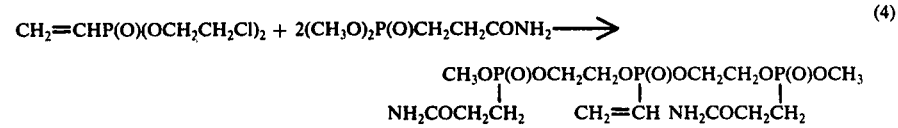

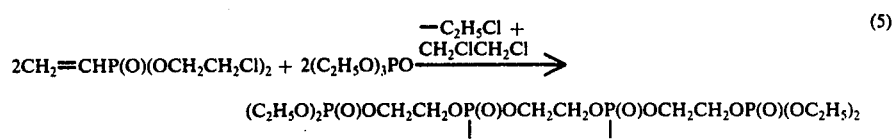

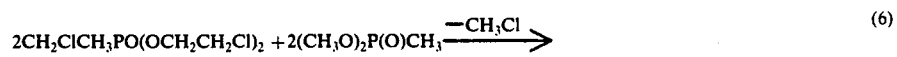

-continued

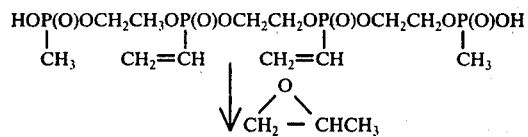

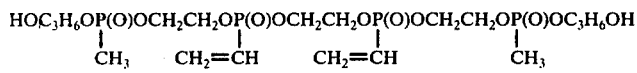

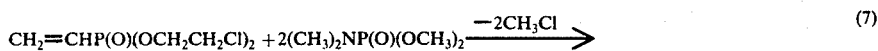 (7)

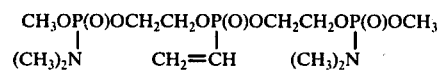

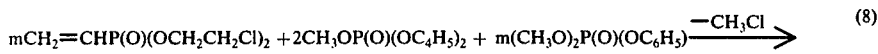 (8)

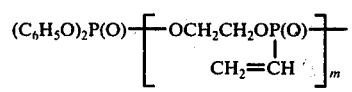

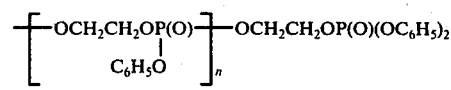

where m ≧ 1 and n = 0 to m

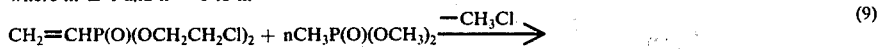 (9)

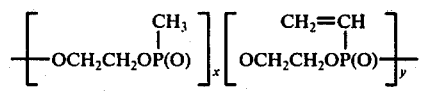

where n > 0 and x and y ≧ 1

The above product formula is only an inexact representation of the product structure. The end groups may, on stoichiometric grounds, be either $CH_3OP(O)(CH_3)$— or $ClCH_2CH_2OP(O)(CH=CH_2)$—, and one or both can be present in the product. It is not known if the methylphosphonate and vinylphosphonate repeating units are distributed randomly, alternatively or in blocks. Acidic by-product structures also known to be present in the actual product are not represented by the formula.

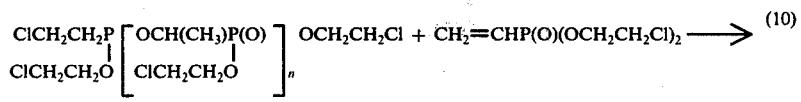 (10)

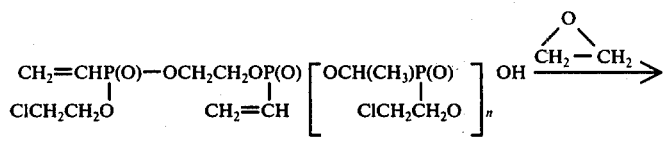

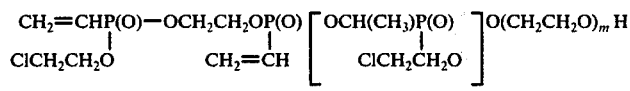

where m = 1 to about 5
where n = 0 to 10

 (11)

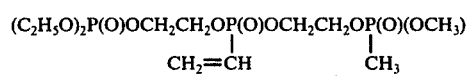

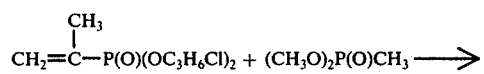 (12)

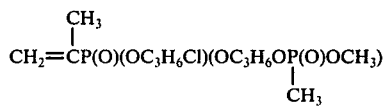

where $-C_3H_6-$ can be $-CH_2CH(CH_3)-$ and/or $-CH(CH_3)CH_2-$

As may be seen from a study of the above given reactions, by having an exact 1:1 reactant ratio of $CH_2=CHPO(OCH_2CH_2Cl)_2$ and $(RO)_2P(O)X$ and running the reaction to completion, a high molecular weight polymer product can be obtained. Alternatively, by having an excess of either reactant, the chain length of the product can be controlled and its end groups will be primarily those derived from the reactant which is present in excess.

As has previously been noted, a particularly preferred group of products coming within the scope of this invention are those compounds wherein ROP(O)XY is dimethyl methylphosphonate, i.e. $(CH_3O)_2P(O)CH_3$, and the resultant products are, therefore copolycondensates which, depending on the reactant ratio, have varying proportions of

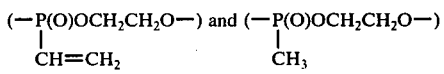

groups as their repeating units $-P(O)(CH_3)OCH_3)$ and/or $-P(O)-(CH=CH_2)(OCH_2CH_2Cl)$ groups as their end groups. The typical products of this preferred class as made by the polycondensation of bis(2-chloroethyl) vinylphosphonate with dimethyl methyphosphonate in ratios from about 1:10 to about 10:1. These products are mixtures of polymers and oligomers of various chain lengths with various permutations and combinations of the above-mentioned repeating units and end groups. These products are generally inseparable by any practical means and are, therefore, best defined by their method of preparation.

When the ratio of dimethyl methylphosphonate to bis(2-chloroethyl) vinylphosphonate is 2:1, or greater, the principal product is easily shown by nmr, i.e. nuclear magnetic resonance, to be mainly the compound:

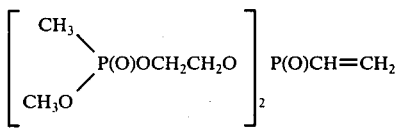

with any dimethyl methylphosphonate which is in excess of the stoichiometric 2:1 ratio remaining unreacted but serving, by mass action, to repress the formation of higher molecular weight oligomers.

In general, this preferred group of copolycondensates of bis(2-chloroethyl) vinylphosphonate and dimethyl methylphosphonate shows a high level of flame retardant efficacy and outstandingly good hand when used to prepare textile finishes. Careful investigation of this group of products shows a peak of activity at about a 1:1 ratio, with the best products being encompassed within the range of about 2:3 to 3:2, i.e. dimethyl methylphosphonate:bis(2-chloroethyl) vinylphosphonate.

It is to be emphasized at this point that the structures of the novel copolycondensed vinylphosphonates of this invention are quite difficult to specify by means of precise formulae. Thus, the initial co-condensation reaction involving the bis(2-haloethyl) vinylphosphonate and the pentavalent phosphorus ester would be expected, in an idealized sense, to run as follows:

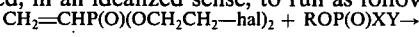

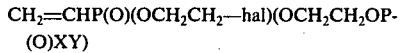

However, even in the simple case where X and Y are not alkoxy, and thus cannot be further reacted, the product tends to be complicated by some reaction of the $-OCH_2CH_2-$hal groups of the reactant. Furthermore, when either or both of X and Y are alkoxy, and thus are reactable in the same sense as RO, additional permutations and combinations become possible and the reaction products are believed to be generally mixtures except in those limiting cases where a sizeable excess of one reactant or the other is utilized.

Moreover, in actual experiments it has been found that acidic groups are demonstrable by titration. Therefore, any formula showing only ester linkage cannot completely represent the product. Thus, titration experiments indicate that P(O)—OH and probably P(O)—O—P(O) groups are present in these products. Furthermore, certain intramolecular reactions also proceed concurrently with the intermolecular polycondensation, to yield cyclic glycol esters containing the group:

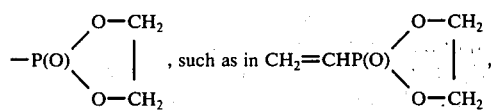

and these cyclic esters are detectable in the reaction mixture by their ability to quickly hydrolyze to titratable acid in water and to react with alcohol to yield neutral esters.

Since these cyclic esters generate acidity upon contact with water, where the products of the invention are to be employed in water solution or are expected to come in contact with moisture, it is often preferable to add an amount of an alkanol, such as methanol to the reaction mixture in an amount sufficient to open up the rings of the cyclic glycol ester so as to yield neutral ester products.

As has been noted, the novel copolycondensed vinylphosphonates of this invention will often contain acid structures resulting from side reactions. Or, such acid structures may be deliberately introduced into these products if a 2-haloethylphosphonate is used as a reactant for their preparation. Accordingly, in a further aspect of the process of this invention, the acid groups which are present in these copolycondensates may be neutralized with an epoxide reagent thereby converting them into hydroxyalkyl ester groups. Thus, in many instances, such acid groups may interfere, to a substantial degree, with the utility of the copolycondensed vinylphosphonates. For example, they may retard the curing rate when they are utilized in the preparation of polyester resins and may impart relatively inferior moisture resistance and weathering properties. In textile finishing applications, acidity can be helpful in some situations such as where an aminoplast co-reactant is to be cured into the finish, or it can be injurious in other situations such as where soft fabrics, e.g. cotton flannels, are to be finished without adverse effect on their tactile quality, i.e. their hand.

Thus, the removal of this acidity can, if desired, be brought about by neutralizing these acidic copolycondensates by means of various reactions with a neutralizing amount, i.e. an amount which is at least effective to neutralize substantially all of the acidic groups, of an alkylating reagent. Suitable alkylating reagents include trialkyl orthoformates and epoxides with the latter being preferred because of their low cost and high efficiency. Such epoxide reagents include ethylene, propylene, butylene, octylene, and styrene oxides, epichlorohydrin, epibromohydrin, glycidol, glycidyl ethers such as the diglycidyl ether of isopropylidenediphenol, butadiene diepoxide, vinylcyclohexene diepoxide, 3,3,3-trichloro-1,2-epoxypropane, and glycidyl esters such as glycidyl methacrylate and glycidyl acrylate. Preferred for use in preparing the fire retardant textile especially cellulosic finishes of this invention are the copolycondensed vinylphosphonates which have been neutralized by being reacted with ethylene or propylene oxide, epichlorohydrin or the diglycidyl ether of isopropylidenediphenol. The reaction may be run at a temperature of from about 25° to 225° C., preferably at about 50° to 150° C., over a period of from about 0.1 to 24 hours. The reaction is usually terminated when an analytical determination of the remaining acid groups in the copolycondensate reveals that they are present in an insignificant level. Thus, for most practical purposes, an acid number of about 10 mg KOH/gm, or less, is the equivalent of neutrality. The precise amount of acidity which is considered insignificant will, of course, depend upon the particular use to which the neutralized co-condensate is to be put. Any unreacted epoxide reagent dissolved in the reaction product may then be removed by purging the system with nitrogen and/or by applying vacuum.

The thus produced neutralized copolycondensed vinylphosphonates are syrups whose viscosity increases with an increase in their degree of condensation. Although these neutralized condensates can be prepared so as to have 20 or more phosphorus atoms per molecule, such products are extremely viscous and are not ordinarily as useful as those wherein there are from about two to about 10 phosphorus atoms per molecule since the latter are more conveniently utilized in the textile finishing process of this invention. Thus, the most preferred neutralized copolycondensates are those which possess an average total of from about two to about 10, phosphorus atoms per average copolycondensate molecule. A discussion of theoretical aspects of the neutralization, with epoxide reagents, of polycondensed vinylphosphonates may be found in the article by Kafengauz et al on page 73 of the April, 1967 issue of Soviet Plastics.

It should also be noted, at this point, that the copolycondensation reaction of this invention may be carried out either simultaneously or consecutively with the homopolycondensation of a bis(2-haloethyl) vinylphosphonate, preferably bis(2-chloroethyl) vinylphosphonate, which is conducted at a temperature sufficient to evolve an ethylene dihalide, e.g. about 140°–250° C., preferably about 160°–220° C. This possibility allows for many variations in the composition of the products resulting from the process of this invention.

As prepared by means of the above described procedures, the preferred copolycondensed vinylphosphonates of the invention are soluble in many organic solvents as well as in water. Thus, while the use of aqueous solutions comprises the most economical means of application for these flame retardants, they may also, if desired, be applied to a textile substrate while dissolved in any of the organic solvents commonly used in the solvent finishing of textiles including, for example, trichloroethylene, dichloroethane, trichloroethane, perchloroethylene, methylene chloride, etc., and mixtures thereof.

The solutions, either aqueous or organic solvent, containing one or more of the selected cocondensates may be applied to textiles by the use of any desired procedure. It is merely necessary to have the cocondensate evenly absorbed throughout the mass of the textile and/or to apply it to at least one surface thereof by means of any convenient procedure. Thus, the cocondensate may be applied by being sprayed or printed onto one or both surfaces of the textile, by fabric lamination and/or by pigment printing techniques. Or, as is more frequently the case, the textile is passed through or padded with the solution while the latter is being held in a tank or other suitable container. Such a process is commonly referred to as a "padding" technique with the solution being referred to as a "padding bath" or "padding solution".

The concentration of the selected, copolycondensed vinylphosphonate within the padding bath, or other applicable solution, will be dependent upon a number of factors including the nature of the fibers which comprise the textile, the weight and weave of the textile, the degree of flameproofing that is desired in the finished textile, as well as other technical and economic considerations known and understood by those skilled in the art. However, it is generally desirable that the "dry add-on", i.e. the final amount of the resin finish on the textile, should be in the range of from about 5 to 50%, as calculated on the dry weight of the untreated textile. This range of dry add-on will, in turn, provide the thus treated textile with about 0.5 to 10%, preferably about 1-5% of phosphorus as based upon the dry weight of the untreated textile. Again, it is to be stressed that the latter limits are merely illustrative and may be varied so as to provide a textile finishing having any desired degree of flame retardancy.

The thus applied cocondensate may be cured in the wet state or it may be completely or, most preferably, partially dried before curing. The mode of curing in accordance with the process of the invention preferably involves the use of a free radical initiated reaction in order to induce the double bonds, i.e. the ethylenic unsaturation, of the vinyl groups present in the copolycondensed vinylphosphonate to polymerize intermolecularly so as to form a crosslinked, insoluble resin in and/or on the individual fibers which comprise the textile substrate. In this curing reaction, the vinyl groups in the condensate may react with each other and/or with the cellulose. In the latter case, the reaction may be described as "grafting".

Free radical initiation of the desired polymerization reaction may be induced either by the use of those chemical catalysts known as free radical initiators and/or by the use of actinic radiation. Suitable free radical catalysts encompass azo compounds as well as peroxygen compounds. The latter catalysts may be used as part of a so-called redox system containing a chemical reducing agent such as ascorbic acid, a bisulfite or a ferrous salt, etc. in addition to the peroxygen compound. An example of a suitable peroxygen catalyst is hydrogen peroxide, which is often used in a concentration of from about 0.01 to 5%, by weight, of the selected, copolycondensed vinylphosphonate. Where especially rapid catalysis is desired, the use of a redox system, comprising a peroxygen catalyst in combination with one of the above described reducing agents is recommended. These two components of the redox system may be applied to the textile substrate in separate operations in order to prevent premature cure.

Where a cure is induced by the use of a free radical catalyst, the selected catalyst may be conveniently activated by heating up to about 180° C. but, preferably in the range of from about 60° to 160° C. so as to avoid any thermal damage to the textile. Heating may, if desired, be accomplished by the use of steam or hot gases or by conventional oven curing techniques in air or in an inert atmosphere. Alternatively, the catalyst can be activated by applying a reducing agent of the type described hereinabove to the cloth either before or after applying the flame retardant and catalyst. The catalyst may also be activated by actinic radiation.

Generally, the rate of cure of a catalytically initiated cure is adversely influenced by the presence of atmospheric oxygen. Therefore, for an optimum cure rate, it is advantageous to exclude oxygen by use of an inert gas which can be steam, nitrogen, carbon dioxide or the like. A particularly convenient means for accomplishing this effect is to conduct the final drying of the finish at the cure temperature so that the steam being evolved forms an air-excluding blanket. In the textile mill this is easily accomplished by passing the treated textile from the padder over heated metal cylinders or "cans" at such a rate and temperature as to initiate curing while some moisture still remains. However, it has been surprising to find that, in the process of this invention, the rate of cure of the copolycondensed vinylphosphonate is still quite adequate in the presence of atmospheric oxygen. Thus, a more convenient means for curing these novel finishes involves the use of a typical pad-dry technique, i.e. conventional oven curing in air.

Actinic radiation encompasses high energy protons and other particles capable of initiating free radical reactions including ultraviolet light, x-rays, gamma rays, alpha rays, beta rays, i.e. electron beam radiation, and plasma, i.e. a highly ionized gas as obtained, for example, in corona discharges from a high voltage terminal in the presence of an easily ionized gas such as argon. A preferred source of actinic radiation involves the use of an electron beam, i.e. beta radiation, since equipment adaptable for textile mill use is readily available and is eminently suited for rapid, continuous processing. In any event, regardless of the type of actinic radiation that is used, it should be applied in a dosage which is sufficient to initiate polymerization. Thus, in the case of electron beam radiation, suitable dosages are typically in the range of 0.1–10 megarads.

When actinic radiation is used, either alone or in combination with a free radical catalyst, it is necessary to expose the textile to a beam from a radiation source. if desired, this can be done at ambient temperature, in air or in an inert atmosphere, and with great rapidity, e.g. from about 0.1 seconds to several minutes, thus sparing the textile from thermal damage. One advantage of the use of radiation curing is the fact that since catalysts and heating are not required, the textile is generally found not to have undergone any serious degradation of its physical properties such as color, tear strength and abrasion resistance. In addition, a radiation induced cure is generally not as seriously affected by the presence of oxygen in the system as is a chemically induced cure. Moreover, it has been found that by using radiation to affect the cure, the resulting finish will be tightly cured, i.e. extensively crosslinked, so as to provide it with greater durability to laundering and dry cleaning.

The exposure to actinic radiation can be conveniently conducted by passing the textile through the beam which may be produced, for example, by a bank of ultraviolet lamps, corona-discharge points, a cobalt-60 source, an x-ray source or an electron beam source. Reasonably homogeneous radiation flux is desirable where an electron beam is used. Thus, the beam can be transversely scanned across the textile at a rapid rate so as to evenly irradiate all points thereon. If desired, a suitable mechanical arrangement of rollers can be employed so that the treated textile can be made repeatedly pass through the radiation field, thereby facilitating more complete use of the available radiation flux while also obtaining more uniform irradiation.

The use of actinic radiation initiation does not generally require the use of a chemical activator. However, the efficiency of the radiation can frequently be improved by use of such an activator. Suitable activators for this purpose include ketones, such as acetone or benzoin; polycyclic hydrocarbons, such as polyphenyl; and, azo compounds such as azobisisobutyronitrile.

The irradiation of the textile is usually carried out subsequent to the application of the condensate, although in the case of cellulosic fibers which can be iradiated so as to form stable, long lived free radical sites, the cocondensate can be applied subsequent to irradiation whereupon it will proceed to cure by grafting onto the cellulose.

The resulting cure, or polymerization, of the copolycondensed vinylphosphonate, which is induced by either an acid catalyst and/or a free radical catalyst and/or actinic radiation, is believed to take place on the surface of the individual fibers which comprise the textile substrate. However, where the fiber is one which can readily absorb the selected condensate such, for example, as the cellulosic fibers, the polymerization can also take place within the body of the fibers. Moreover, as has been noted, in some cases the resulting polymer network may be grafted, or chemically bonded, onto the textile fiber molecules. However, such grafting is not crucial to the attainment of a curable, flame retardant finish. Grafting can be enhanced, if desired, by pretreating cellulose with ceric salts, ferric salts, various other metal salts, or by xanthation, however, the present process does not require this step.

The process of this invention may, if desired, include the use of other free radical curable, i.e. ethylenically unsaturated, comonomers along with the copolycondensed vinylphosphonate as a means of achieving variations in the properties of the resulting treated textile. The thus added optional comonomers form copolymers with the copolycondensed vinylphosphate during its curing or polymerization. Suitable comonomers for use in conjunction with the cocondensate include;

1. Monomers containing an amide nitrogen such as acrylamide, methacrylamide, N-methylolacrylamide, N-methylolmethacrylamide, diacetonylacrylamide, hydroxymethylolated diacetonylacrylamide, methylenebisacrylamide, triacryloylhexahydrotriazine N-vinylpyrrolidone, and cellulose-grafted N-methylolacrylamide, the use of the latter monomer being disclosed in U.S. Pat. No. 3,434,161. The use of these amide nitrogen containing comonomers at a concentration of up to about six molecules per each vinyl groups of the copolycondensed vinylphosphonate, permits a more economical finish, particularly with cellulosic fibers, since less of the more costly phosphonate monomer needs to be used in order to achieve a given level of flame retardancy. From the latter group of monomers, the use of acrylamide or N-methylolacrylamide is preferred because of their low cost and high efficiency.

It is to be noted that the use of N-methylolacrylamide, N-methylolmethacrylamide or hydroxymethylated diacetonylacrylamide offers some additional advantages in view of the known ability of these monomers to attach to cellulose by acid-catalyzed ether formation. Such attachments can serve to more tightly anchor the finish to the fiber. The requisite catalytic acid for such a reaction is generally present as the result of minor hydrolysis of the vinylphosphonate reagent during curing. However, if this amount of acid is found inadequate, additional catalytic acid can be added in the form of mineral acids such as hydrochloric or phosphonic; organic acids such as citric, lactic, oxalic, or glycolic; or, acidic salts such as amine hydrochlorides, magnesium chloride, zinc nitrate, or ammonium chloride.

2. Monomers containing more than one polymerizable double bond such, for example, as the glycol diacrylates, the glycol dimethacrylates, methylene bisacrylamide, triacryloylhexahydrotriazine, triallyl phosphate, dialkyl allylphosphonates and triallyl cyanurate. By using this class of comonomers, the crosslink density of the resulting finish can be increased, thereby enhancing its durability with respect to wear and laundering.

3. Monomers contributing to flame retardancy, i.e. monomers having phosphorus, bromine or chlorine atoms in their molecules including, for example, vinyl and vinylidene halides such as vinyl chloride, vinyl bromide, vinylidene chloride, vinylidene bromide, vinylidene chlorobromide and chloroprene; triallyl phosphate; diallyl phosphonate; dialkyl vinylphosphonates such as diethyl vinylphosphonate and bis(2-chloroethyl) vinylphosphonate or its polycondensation products.

4. Monomers contributing to surface quality, i.e. "hand", softness, flexibility, smoothness of tactile quality, gloss, soil release, and abrasion resistance, for example hydroxyalkyl, acrylates or methacrylates, alkoxyalkyl acrylates or methacrylates, long-chain alkyl acrylates or methacrylates, vinyl long chain alkyl acrylates or methacrylates, vinyl long-chain alkyl esters, vinyl esters of fatty acids or fluorinated alkanoic acids, acrylic or methacrylic acid, or the like.

When utilized in the process of this invention, the above described optional comonomers can be present in the system in an amount of up to about 6 molecules per each vinyl group of the required copolycondensed vinylphosphonate in the mixture with the aminoplast.

It should be noted, at this point, that the use of the term "crosslinked" in describing the cured, fire retardant resins resulting from the polymerization of the copolycondensed vinylphosphonate in the textile finishing process of this invention will indicate to those skilled in the art that these resins possess a three-dimensional configuration or network rather than a simple linear or branched structure of the type found in non-crosslinked copolymers. Moreover, as used in this disclosure, the term "fire retardant" is intended to refer to that particular property of a material which provides it with a degree of resistance to ignition and burning. Thus, a fire or flame retardant textile is one which has a low level of flammability and flame spread. This property may be conveniently evaluated by means of any of the standard flame retardancy tests.

The textile finishing process of this invention is compatible with a wide variety of other textile finishing operations which can be carried out prior, simultaneous with, or subsequent to the process of this invention. These other operations include application of durable press, softening, anti-static, abrasion resistance, water-repellent, soil-release and anti-microbial finishes as well as bleaching, dyeing, printing, flocking, laminating and texturing. Thus, the finishing formulations of this invention may also optionally contain other types of ingredients known in the textile finishing art. For example, water and soil repellents, optical brighteners and colorants, softening agents such as polyethylene emulsions, hand-modifying agents, buffering agents, pH-controlling agents which may be acidic or basic, emulsified waxes, chlorinated paraffins, polyvinyl chloride, polyvinylidene chloride, homo- and copolymers of the alkyl acrylates and other resinous finishing agents may be added in conjunction with the finishing agents of this invention. And, where an extremely high degree of flame retardance is required, it is possible to employ systems containing antimony oxide and a resinous binder, particularly one containing chlorine, such as a chlorinated paraffin or polyvinyl chloride, along with the copolycondensed vinylphosphonates required in the process of this invention.

Another class of optional additives whose presence may be useful when the novel copolycondensed vinylphosphonates of this invention are used in preparing flame retardant textile finishes are the so called aminoplasts. Thus, the use, in this disclosure, of the term "aminoplast" is meant to denote a nitrogen containing resin which is capable of reacting with itself, with the copolycondensed vinylphosphonate and/or with the textile and which is prepared by the polycondensation of formaldehyde with a compound having at least two reactive amino or amido hydrogen atoms. Exemplary of the aminoplasts applicable for use in the textile finishing process of this invention are methylolureas which may be either straight chained or cyclic, methylolmelamines, methylolcarbamates, methylolurons, methylolamides, methyloltriazines, the methyl esters of the above listed methylol compounds, methylolated acid amides, dimethyl hydroxymethylcarbamoylethylphosphonate, urea-glyoxal condensation products, urea-glyoxal-formaldehyde condensation products, N-methylolated O-alkyl carbamates. Preferred aminoplasts include tris(-methoxymethyl) melamine, as sold by the American Cyanamid Co. under the trademark "AEROTEX M-3"; partially methylolated methoxymethyl melamine, as sold by the American Cyanamide Co. under the trademark "AEROTEX 23 SPECIAL"; dimethylolethylene urea; dimethyloldihydroxyethylene urea, dimethylol ethyl carbamate and dimethoxymethyl uron.

By combining one or more aminoplasts with the novel copolycondensed vinylphosphonates of this invention, it is possible, if desired, to completely avoid or minimize the need for utilizing expensive and often times toxic comonomers, such as acrylamide, in preparing fire retardant textile finishes. Moreover, these novel finishes can be cured at relatively low temperatures, e.g. at 275°–280° F., and with relatively lower levels of catalysts than would ordinarily be expected. In addition, the presence of the aminoplast in these finishes serves as a buffer which prevents discoloration and tenderization of cotton fabrics thereby eliminating the need for any extraneously added buffers such as urea. These aminoplasts may be used in a concentration in the range of from about 10 to 600%, preferably about 25–300%, by weight, of the copolycondensed vinylphosphonate. In general, increasing the aminoplast level allows one to use less of the copolycondensed vinylphosphonate in order to achieve a given degree of flame retardancy, particularly with cellulosic fabrics. Where an aminoplast or an amide comonomer is employed, the flame retardant effect of the finish may be further enhanced by inclusion of tetrakis(hydroxymethyl) phosphonium chloride or hydroxide, or tris(hydroxymethyl) phosphine in the formulation.

All types of textiles may be treated by means of the process in this invention so as to provide them with durable, fire retardant finishes. Thus, one may treat textiles derived from natural fibers such as cotton, wool, silk, sisal, jute, hemp and linen and from synthetic fibers including nylon and other polyamides; polyolefins such as polypropylene; polyesters such as polyethylene terephthalate; cellulosics such as rayon, cellulose acetate and triacetate; fiber glass; acrylics and modacrylics, i.e. fibers based on acrylonitrile copolymers; saran fibers, i.e. fibers based on vinylidene chloride copolymers; nytril fibers, i.e. fibers based on vinylidene dinitrile copolymers; rubber based fibers; spandex fibers, i.e. fibers based on a segmented polyurethane; vinyl fibers, i.e. fibers based on vinyl alcohol copolymers; vinyon fibers, i.e. fibers based on vinyl chloride copolymers; and, metallic fibers. Textiles derived from blends of any of the above listed natural and/or synthetic fibers may also be treated by means of the process of this invention.

As used in this disclosure, the term "textile" or "textiles" is meant to encompass woven or knitted fabrics as well as non-woven fabrics which consist of continuous and/or discontinuous fibers bonded so as to form a fabric by mechanical entanglement, thermal interfiber bonding or by the use of adhesive or bonding substances. Such non-woven fabrics may contain as much as 100% of wood pulp as well as conventional textile fibers in which case part of the bonding process is achieved by means of hydrogen bonding between the cellulosic pulp fibers. In non-woven fabrics, the finishing agents of this invention can function not only as flame retardant finishes but can also contribute to the interfiber bonding resin component. This dual role can also be played by the finishing agents of this invention in fabric laminates and in flocked fabrics where the finishing agent can at the same time serve as the interlaminar bonding agent or flocking adhesive as well as the flame retardant. In both of these systems, i.e. non-woven fabrics and laminated fabrics, the finishing agents of this invention can also be blended with the usual bonding agents such as, for example, as acrylic emulsion polymers, vinyl acetate homo- and copolymer emulsions, styrene-butadiene rubber emulsions, urethane resin emulsions, polyvinyl chloride emulsions, vinyl chloride alkyl acrylate copolymer emulsions, polyacrylates modified by vinyl carboxylic acid comonomers and the like.

It should also be noted, at this point, that in addition to being used to provide flame retardant finishes for textiles, the copolycondensed vinylphosphonates of this invention can be used for flameproofing a variety of otherwise flammable polymeric substrates such as cellulose in the form of paper, wood, plywood, chipboard, jute, batting and the like; urethane foams, rebonded urethane coatings, and elastomers; aminoplast resins and phenolic resins as well as their composites with paper, wood flour and the like; alkyd coatings and moldings resins; and, paints and varnishes derived from natural or synthetic resins. In such applications the products of the invention can be employed either as additives or as reactive materials. As reactive flame retardants, the products of this invention may be copolymerized by means of their vinyl groups using vinyl polymerization initiators as described hereinabove. Moreover, they may be reacted into the form of polymers by the nucleophilic addition of amino, hydroxy, or sulfhydryl groups to the double bonds. In addition, the epoxide-neutralized products of the invention have reactible hydroxyalkyl end groups which can be reacted with acylating groups, such as isocyanate groups in order to produce polyesters.

It should also be noted that halogens, e.g. bromine and chlorine, can be added to the double bonds of bis(2-chloroethyl) vinylphosphonate, the homopolycondensation product thereof, or to the copolycondensation products of the present invention in order to prepare 1,2-dihaloethylphosphonates which are useful as flame retardant additives for plastics, such as polyester resins, vinyl resins, and the like.

Another application in which these copolycondensed vinylphosphonates are particularly useful is in the preparation of flame retardant unsaturated polyesters wherein they function as reactive flame retardant intermediates. The unsaturated polyesters are characterized by vinyl unsaturation in the polyester backbone which permits their subsequent hardening or curing by copolymerization with a reactive monomer in which the polyester constituent has been dissolved. The unsaturated polyesters are made by heating an agitated mixture of glycols, e.g. propylene- or diethylene glycol, an unsaturated dibasic acid or anhydride, e.g. fumaric acid or maleic anhydride and, sometimes in order to control the reaction and modify properties, a saturated dibasic acid or anhydride, e.g. isophthalic acid or phthalic anhydride. After removal of water and cooling, the fluid polyester may be dissolved in a reactive monomer in the same reaction vessel, or it may be shipped to users who add the monomer and catalyst in their factories. Styrene is most widely used as the reactive monomer while diallyl phthalate, diallyl isophthalate and triallyl cyanurate are also sometimes used. Peroxide catalysts are generally used for the final copolymerization reaction. These unsaturated polyesters are thermosetting and are most widely used in reinforced plastics and in the potting of electrical components. Thus, one or more of the novel copolycondensates of this invention may be introduced into the system prior to the final copolymerization reaction in a concentration of from about 2 to 90%, as based upon the weight of the total resin composition.

Surprisingly, the degree of flame retardancy thus imparted is in excess of that imparted by monomeric or homopolycondensed bis-2-chloroethyl vinylphosphonate.

The following examples will further illustrate the embodiment of this invention. In these examples, all parts given are by weight unless otherwise noted.

EXAMPLE I

This example illustrates the preparation of one of the novel copolycondensates of this invention which, in this case, comprises the copolycondensate of 7 moles of dimethyl methylphosphonate and 6 moles of bis(2-chloroethyl) vinylphosphonate.

Part A

In a reactor fitted with a stirrer, vertical reflux condenser, and effluent line from the latter to a dry-ice cooled receiver, there is placed 2,796 gms. (6 moles) of bis(2-chloroethyl) vinylphosphonate, 1,736 gms. (7 moles) of dimethyl methylphosphonate and 10 gms of sodium carbonate. The reactor is stirred and heated. At 135°–140° C. the evolution of methyl chloride begins and the temperature is then raised over about 5 hours to 190° C. and held at this temperature until the rate of collection of distillate, i.e. of methyl chloride and a minor percentage of ethylene dichloride, in the dry-ice trap becomes less than 10 cc/hour. The reaction mixture is then sparged breifly with nitrogen. By titration in water, the 3,317 gms. of residual product is found to contain 1.4 millequivalents per gm. of total acidity.

Part B

The above described reaction product is treated at 100°–110° C. with 182 gms. of methanol over 1 hour, thus reducing the acidity to 0.4 melliequivalents per gm. The acidity is then reduced to a neglible level, i.e. to less than 0.1 milliequivalents per gm, by passing in ethylene oxide over 3 hours at 100°–110° C. The resultant product, after brief sparging with nitrogen to remove dissolved ethylene oxide, comprises 3,498 gms. of a pale yellowish clear liquid, $n_D^{25}$ 1.4735, acid no. 0.42 mg. KOH/g, which is soluble in water and has a chlorine content of only 0.42%. As expected, the nuclear magnetic resonance spectrum shows about 1.16 $CH_3P(O)$ groups per $CH_2=CH-P(O)$ groups.

EXAMPLE II

This example illustrates the preparation of one of the novel copolycondensates of this invention which, in this case, comprises the copolycondensate of 2 moles of dimethyl methylphosphonate and 1 mole of bis(2-chloroethyl) vinylphosphonate. It also demonstrates the use of the resulting copolycondensate in the preparation of a flame retardant polymer.

A mixture of 1 mole (233 gms) of bis(2-chloroethyl) vinylphosphonate, 2 moles (248 gms.) of dimethyl methylphosphonate, 1 gm. of sodium carbonate and 10 mg. of di-tert-butylhydroquinone is heated and stirred at 187°–197° C. for 2 hours allowing 102 gms of volatiles, primarily methyl chloride, to distill off. The reaction mixture is then subjected to vacuum distillation at a temperature of 183° C., a vapor temperature of 126° C. while under 20 mm pressure with the distillate comprising 65 gms. of unreacted dimethyl methylphosphonate. The residual product is found by titration of a sample in water to have 1 milliequivalent of acid-yielding components per gram. The addition of 20 gms. of methanol followed by warming at 90°–100° C. for 5 hours reduces the acidity to 0.29 milliequivalent per gram, whereupon the introduction of ethylene oxide at 120° C. over a 1 hour period further reduces the acidity to nil, i.e. to a neutral response to Bromphenol blue indicator.

The product is a water-soluble syrup, the infrared spectrum of which shows vinylphosphonate, methylphosphonate, hydroxyethyl, and ethylenedioxy structures. Polymerization of this monomeric product by exposure to ultraviolet light yields a rubbery solid which cannot be ignited with the flame from a bunsen burner.

A repetition of the above described preparative procedure using a 100% excess (496 gms.) of dimethyl methylphosphonate, the excess being recovered by vacuum distillation, yields a water soluble, colorless liquid having, by nmr spectroscopy, 2 $CH_3O-P$ and 2 $CH_3P$ groups per $CH_2=CHP$ group, thus indicating that it is substantially pure $(CH_3O)(CH_3)P(O)OCH_2$ $CH_2OP(O)-(CH=CH_2)OCH_2CH_2OP(O)$ $(CH_3)(OCH_3)$.

EXAMPLE III

This example illustrates the preparation of one of the novel copolycondensates of this invention which, in this case, comprises the copolycondensate of 1 mole of bis(2-chloroethyl) vinylphosphonate with 1.33 moles of trimethyl phosphate. The polymerization of this copolycondensate is also demonstrated.

A mixture of 233 gms. (1 mole) of bis(2-chloroethyl) vinylphosphonate, 187 gms. (1.33 moles) of trimethyl phosphate, 1 gm. of sodium carbonate and 0.1 gm. of hydroquinone is heated at 159° to 196° C. over 5 hours while collecting about 2 moles of methyl chloride. The residual product is briefly purged with a stream of dry nitrogen, thereby causing another 3 gms. of distillate to be removed. The residual product contains less than 0.5% Cl and has an acidity of 0.4 milliequivalent/gm. Heating for 1 hour at 100° C. with 20 gms of trimethyl orthoformate and 10 gms. of methanol, reduces the acidity to 0.21 milliequivalent/gm. The product is a nearly colorless water-soluble syrup, $n_D^{20}$ 1.4700, having an infrared and nmr spectrum consistant with the structure of a copolyester of a vinylphosphonate and methylphosphonate linked by $P-O-CH_2CH_2-OP$ groups and terminated by $P-OCH_3$ groups.

This monomer, when exposed to the radiation from a high pressure mercury arc lamp for 12 hours, polymerizes to a colorless elastomeric solid which resists ignition when held in a Bunsen burner flame.

EXAMPLE IV

This example illustrates the preparation of one of the novel copolycondensates of this invention which, in this case, comprises the copolycondensate of 2 moles of bis(2-chloroethyl) vinylphosphonate and 2 moles of tris(2-chloroethyl) phosphate. It also demonstrates the use of the resulting copolycondensate in the preparation of a flame retardant polymer.

A mixture of 572 gms. (2 moles), of tris(2-chloroethyl) phosphate, 466 gms. (2 moles) of bis(2-chloroethyl) vinylphosphonate, 4 gms. of sodium carbonate, and 20 mg. of tertbutylhydroquinone is heated and stirred at 181°–181° C. over 4 hours, allowing 307 gms. (about 3 moles) of ethylene dichloride to distill off. The residual liquid is found, by titration, to contain 0.3 moles of acid and/or rapidly hydrolyzed ester or anhydride, which is neutralized by introducing ethylene oxide at 120°-130° C. The resultant product is a viscous liquid containing 17% P.

When a sample of this product is polymerized, in bulk, by exposure to a mercury vapor lamp for one day, the resultant polymer is found to be a clear, non-flammable elastomer. Under similar conditions, the polymerization of the homopolycondensate of bis(2- chloroethyl) vinylphosphonate yields a brittle, hard solid having no elastic properties.

EXAMPLE V

This example illustrates the use, in preparing flame retardant textile finishes, of a number of copolycondensates containing varying ratios of dimethyl methylphosphonate and bis(2-chloroethyl) vinylphosphonate.

The copolycondensates used in this experiment are prepared by means of the procedures described in Example I and II and their respective dimethyl methylphosphonate:bis(2-chloroethyl) vinylphosphonate ratios are as follows:

| Copolycondensate No. | Dimethyl Methylphosphonate: Bis(2-chloroethyl) Vinylphosphonate Ratio |
|---|---|
| 3 | 1.0 |
| 4 | 1.13 |
| 5 | 1.33 |
| 6 | 1.5 |
| 7 | 2.0 |

As controls for this experiment, there are utilized:

Control No. 1 — The homopolycondensate of bis(2-chloroethyl) vinylphosphonate having a degree of condensation of 2.5 whose use is described in Bath No. 4 of Example VII; and, Control No. 2 — A homopolycondensate of bis(2-chloroethyl) vinylphosphonate having a degree of condensation of ~8.0.

Samples of cotton flannel cloth having a weight of 3.5 oz/sq. yard are padded through baths containing each of the above described copolycondensates and controls, cured at 300° F. for 5 minutes and then subjected to a series of evaluations. The following table provides a description of the composition of each of the padding baths.

| Bath No. | 1 | 2 | 3 | 4 | 5 | 6 | 7 | 8 | 9 |
|---|---|---|---|---|---|---|---|---|---|
| | | | | %, By Weight, In Bath | | | | | |
| Water | 47 | 47 | 47 | 47 | 49 | 46.5 | 43 | 43 | 43 |
| Octylphenoxypolyethyleneoxyethanol (10%, by weight, solids) | 1 | 1 | 1 | 1 | 1 | 1 | 1 | 1 | 1 |
| Copolycondensate No. 1 (100%, by weight, solids) | | | 20 | | | | | | |
| Copolycondensate No. 2 (100%, by weight, solids) | | | | 20 | | | | | |
| Copolycondensate No. 3 (100%, by weight, solids) | | | | | 18 | | | | |
| Copolycondensate No. 4 (100%, by weight, solids) | | | | | | 20 | | | |
| Copolycondensate No. 5 (100%, by weight, solids) | | | | | | | 22 | | |
| Copolycondensate No. 6 (100%, by weight, solids) | | | | | | | | 22 | |
| Copolycondensate No. 7 (100%, by weight, solids) | | | | | | | | | 22 |
| Control No. 1 100%, by wt. solids) | 20 | | | | | | | | |
| Control No. 2 (100%, by weight, solids) | | 20 | | | | | | | |
| N-methylolacrylamide (60%, by wt. solids) | 22 | 22 | 22 | 22 | 20 | 22.5 | 24 | 24 | 24 |
| Potassium Persulfate (5%, by weight, solids) | 10 | 10 | 10 | 10 | 10 | 10 | 10 | 10 | 10 |
| pH of Bath | 5.1 | 5.33 | 5.58 | 5.45 | 2.3 | 5.0 | 4.8 | 2.0 | 5.3 |

The following table provides the results of the various evaluation procedures which are conducted on the resulting treated textile samples:

| | Samples Tested in Bath No.: | | | | | | | | |
|---|---|---|---|---|---|---|---|---|---|
| | 1 | 2 | 3 | 4 | 5 | 6 | 7 | 8 | 9 |
| LOI[1] | | | | | | | | | |
| Before Washing | 28.12 | 27.65 | 30.44 | 31.11 | 29.4 | 31.4 | 31.18 | 30.0 | 32.3 |
| After 10 DW [3] | 23.97 | 25.88 | 27.34 | 27.45 | 28.4 | 28.0 | 27.3 | 27.0 | 25.5 |
| Vertical Char Length[2](in) | | | | | | | | | |
| Before Washing | 6.25 | 4 | 3.5 | 3.5 | 4.0 | 3.25 | 3.25 | 4.0 | 3.25 |
| After 10 DW | BEL[1] | BEL | 3.5 | 3.5 | 3.75 | 3.5 | 2.75 | 4.75 | 6.75 |

-continued

|  | Samples Tested in Bath No.: | | | | | | | | |
|---|---|---|---|---|---|---|---|---|---|
|  | 1 | 2 | 3 | 4 | 5 | 6 | 7 | 8 | 9 |
| % Add-On [5] | 19.9 | 23.2 | 24.2 | 22.4 | 21.0 | 20.9 | 20.9 | 21.6 | 19.4 |
| Hand [6] |  |  |  |  |  |  |  |  |  |
| After 1 HW [7] | 2 | 4 | 3.5 | 3.0 | 2.5 | 2.0 | 2.0 | 1.5 | 1.5 |
| After 10 DW | 2 | 3 | 2.5 | 2.5 | 1.5 | 2.0 | 1.5 | 1.0 | 1.5 |

[1]LOI = see discussion in Example VII.
[2]Vertical char length = see discussion in Example VII.
[3]DW = detergent washes as described in Example VII.
[4]BEL = burned over its entire length.
[5]% Add-On = the amount by weight, expressed as a percentage, of chemicals applied to the fabric as based on the weight of the untreated fabric.
[6]Hand = a subjective evaluation of the tactile quality of the treated fabric wherein an assigned value of 1 is equal to untreated fabric, 2 is marginally firmer, 3 is slightly firmer but can be corrected with additives, 4 is significantly firmer and 5 is stiff and boardy.
[7]HW = a wash cycle in a home washing machine at 60° C. with 8 towels added for ballast to simulate a typical after wash treatment in a textile finishing operation.

The above data reveal that the novel copolycondensates of this invention provide textiles with a degree of flame retardency which is far superior to that which is attained with the homopolycondensate controls, i.e. with Baths Nos. 1 and 2. Moreover this data also demonstrate that, with the preferred dimethyl methylphosphonate:bis(2-chloroethyl) vinylphosphonate copolycondensates, peak flame retardancy activity is achieved with a dimethyl methylphosphonate:bis(2-chloroethyl) vinylphosphonate ratio of about 1:1 with the best products being encompassed within the ratio of from about 2:3 to 3:2.

EXAMPLE VI

This example illustrates the preparation of one of the novel copolycondensed vinylphosphonates of this invention which, in this case, is prepared by means of the co-condensation of two moles of trimethyl phosphate with one mole of bis(2-chloroethyl) vinylphosphonate.

Part A

A mixture of 2 moles (280 gms.) of trimethyl phosphate 1 mole (233 gms.) of bis(2-chloroethyl) vinylphosphonate, 1 gm. of sodium carbonate as a catalyst and 0.1 gm. of di-tert-butylhydroquinone as a polymerization inhibitor is heated at 178°-180° C. for about 7 hours, until substantially the theoretical amount of methyl chloride by-product (2 moles, 101 gms.) is collected in a dry ice cooled trap. The residual product is a colorless syrup, soluble in $H_2O$, and its infrared spectrum is consistent with the structure $CH_2=CHP[CH_2CH_2OP(O)(OCH_3)_2]$ except for the presence of OH bonds. Titration of the product in aqueous medium shows 1.1 milliequivalents of acid or acid-yielding compounds per gram. Heating the product with 25 g. of trimethyl orthoformate at 100° C for 1 hour, is partially successful in reducing the acidity to 0.3 milliequivalents per gram. The product has a refractive index of 1.4460 ($n_D^{25}$). Nuclear magnetic resonance shows 2—$OCH_2CH_2O$— groups and 5.4 $CH_3$—O—P groups per $CH_2=CH—P$ group, approximating the structure $CH_2=CHP(O)[OCH_2CH_2OP(O)(OCH_3)_2]_2$.

The following co-condensation reactions are prepared by means of a reaction procedure comparable to that set forth in Part A, hereinabove.

Part B — The reaction between 2 moles of bis(2-chloroethyl) vinylphosphonate and 4 moles of triethyl phosphate evolving principally ethyl chloride and a small amount of ethylene dichloride. A chlorine-free, water-soluble product remains;

Part C — The reaction between 3 moles of bis(2-chloroethyl) vinylphosphonate and 4 moles of dimethyl methylphosphonate, evolving principally methyl chloride and a small amount of ethylene dichloride; and, Part D — The reaction between 3 moles of bis(2-chloroethyl) vinylphosphonate and 4 moles of tris(2-chloroethyl) phosphate which, in this case, evolves ethylene dichloride as the volatile product.

EXAMPLE VII

This example illustrates the preparation of durable, fire retardant textile finishes with a number of the copolycondensed vinylphosphonates of this invention. It also demonstrates the superiority of these finishes when compared with the finishes derived from a homopolycondensed vinylphosphonate.

A series of four aqueous padding baths are prepared each of which contains 33%, by weight, of a 60% aqueous solution of N-methylolacrylamide, 0.4% by weight, of octylphenoxypolyethyleneoxyethanol as a wetting agent, 0.5%, by weight, of potassium persulfate as a catalyst and 30% by weight, respectively, of each of the following vinylphosphonate condensates:

Bath No. 1 — The copolycondensed vinylphosphonate whose preparation is described in Part A of Example VI;

Bath No. 2 — The copolycondensed vinylphosphonate whose preparation is described in Part B of Example VI;

Bath No. 3 — The copolycondensed vinylphosphonate whose preparation is described in Part C of Example VI; and Bath No. 4 — A homopolycondensed vinylphosphonate as prepared by means of the procedure described in Part A of Example VI in copending application Ser. No. 153,075, filed June 14, 1971, whereby a total of 8 moles (1,864 gms.) of bis(2-chloroethyl) vinylphosphonate, 8 gms. of sodium carbonate and 0.2 gms. of t-butylhydroquinone are heated at a temperature of 170°-185° C. for 3 hours and then sparged with nitrogen gas until a total of 475 gms. of ethylene dichloride has been distilled off. This corresponds to the formation of a condensation product having the idealized average formula:

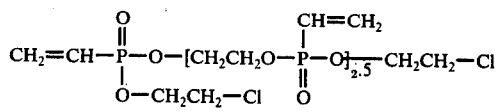

Samples of cotton flannel coth having a weight of 3.5 oz./sq. yard are padded through each of the above described baths, cured at 280°-300° F. whereupon they are then subjected to a hot water, i.e. 60° C., wash followed by a series of 10 hot water, i.e. 60° C., detergent washes in a home washing machine containing 50 grams of "TIDE XK", a strong detergent sold by the Proctor & Gamble Co., and 200 parts per million of water hardness (calculated as CaCO₃ using Mg(NO₃)₂.6H₂O and Ca(NO₃)₂.4H₂O) and eight bath towels as ballast. The flammability of the thus treated cloths is evaluated by means of the Limiting Oxygen Index (LOI) test as well as by means of the Vertical char length test. The LOI test is set forth in the procedure described by Fenimore and Martin in the Nov., 1966 issue of Modern Plastics as well as in ASTM D-2863. In brief, this procedure directly relates flame retardancy to a measurement of the minimum percentage concentration of oxygen in an oxygen:nitrogen mixture which permits the sample to burn; the LOI being calculated as follows:

$$LOI = \frac{[O_2]}{[O_2] + [N_2]} \times 100$$

Thus, a higher LOI is indicative of a higher degree of flame retardancy with a value of about 26–27 being considered a commercially useful degree of flame retardancy as it is generally sufficient to provide self-extinguishing properties as shown by the vertical char test described below.

In the vertical char length test, the complete details of which are described in the Federal Flammability Standard of July 27, 1971, (35 Federal Register 146), a strip of the finished cloth is suspended vertically so that its lower edge is maintained ¾ inch above the top of a Bunsen burner having a 1.5 inch high flame for a period of 3 seconds. The length of the resulting char, in inches, is then measured upward from the base of the strip. Thus, a shorter char length of about 5 to 7 inches is indicative of a greater degree of fire retardancy while a char length of longer than about 10 inches is unacceptable for most applications.

As a control for this experiment, an untreated sample of the cotton flannel cloth is utilized The data obtained from each of the above described test procedures is set forth in the following table:

|  | Fabric Treated in Bath No. | | | | |
|---|---|---|---|---|---|
|  | 1 | 2 | 3 | 4 | Control |
| LOI | 29.09 | 31.94 | 31.53 | 26.32 | 18–19 |
| Vertical Char Length | — | 3" | 3" | 6.25" | BEL* |

*Burned over its entire length.

In another series of evaluations, Bath No. 3 and Bath No. 4 are, in this instance, each modified by substituting 20%, by weight, of acrylamide for the 33%, by weight, of N-methylolacrylamide. Cotton flannel cloth treated in this version of Bath No. 3 is found to have a char length of 3.5 inches whereas the cloth treated in the modification of Bath No. 4, i.e. the bath containing a homopolycondensed vinylphosphonate, is found to be far more flammable having char length of 6.75 inches.

The results of the above described evaluations are, therefore, clearly indicative of the superior flame retardant properties displayed by the textile finishes derived from the novel copolycondensed vinylphosphonates of this invention as compared with a textile finish derived from a hompolycondensed vinylphosphonate.

EXAMPLE VIII

This example illustrates the effect of various types of neutralization treatments upon the properties of the textile finishes derived from the novel copolycondensates of this invention.

In this experiment, there are used a number of 3:4 bis(2-chloroethyl) vinylphosphonate:dimethyl methylphosphonate copolycondensates which differ only in the manner of their neutralization. These copolycondensates are:
  A. The unmodified reaction product, as prepared by means of the procedure of Part A of Example I, having 1.33 meq. acidity/gm.
  B. The product resulting from the treatment of 1,061 gms. of (A) with 67 gms. of methanol at 90°–100° C. for 20 hours and having 0.56 meq. acidity/gm.
  C. The product resulting from treatment of copolycondensate (B) with ethylene oxide at 120° C. until neutral.

Samples of 3.5 oz./yd.² cotton flannel cloth are padded in solutions containing 21% of copolycondensates A, B and C, respectively, along with 23% of a 60% aqueous solution of N-methylolacrylamide and 0.5 gms. of potassium persulfate as a curing catalyst. The cloth is dried, cured at 300° F. for 5 minutes and then washed with hot water. The hand, i.e. the tactile quality, of the resulting dried fabrics is evaluated with the following results being noted:

| Fabric Treated With Copolycondensate | Description of Hand |
|---|---|
| (A) | Firm hard, unacceptable |
| (B) | Moderately firm hand, borderline acceptability |
| (C) | Only slightly firmer than untreated, completely acceptable |

The above given results serve to indicate that improved results are obtained when textile finishes are prepared from the copolycondensates of this invention which have been neutralized especially by reaction with an alkylene oxide.

EXAMPLE IX

This example illustrates the preparation of a variety of the novel copolycondensates of this invention.

The following table provides a description of the reactants, process variables, products and by-products involved in a number of copolycondensation reactions which are carried out by means of procedures comparable to those shown in Examples I-IV, hereinabove.

| Vinylphosphonate | ROP(O)XY | Mole Ratio ROP(O)XY to Vinyl-phosphonate | Catalyst | Temperature (°C) | Main Volatile Product(s) | Predominant (average) Structure in Residual Product |
|---|---|---|---|---|---|---|
| $CH_2=CHP(OCH_2CH_2Cl)_2$ <br> O=  | $(C_2H_5O)_3P=O$ | 2 | 0.1% LiCl | 150–200° | $C_2H_5Cl$, $ClCH_2CH_2Cl$ | $CH_2=CH$ <br> \| <br> $(C_2H_5O)_2P(O)OCH_2CH_2OP(O)$ —O— |
| " | $(CH_3O)_2P-CH_2OCH_3$ <br> O= | 2 | 0.2% $Na_2CO_3$ | 140–160° | mostly $CH_3Cl$ | $(C_2H_5O_2P(O)OCH_2CH_2$ <br> \| <br> $(CH_3O)(CH_3OCH_2)P(O)OCH_2CH_2$ —O— |
| " | $(CH_2BrCHBrCH_2O)_3PO$ | 1 | 0.2% $Et_4NBr$ | 190–210° | mixture of ethylene dihalides & trihalopropanes | $(CH_3O)(CH_3OCH_2)P(O)OCH_2CH_2OP(O)$ <br> \| <br> $CH_2=CH$ |
| " | $(CH_3O)_2P(O)N(CH_3)_2$ | 1 | 0.1% $Et_3N$ | 120–160° | $CH_3Cl$ and some $CH_2ClCH_2Cl$ | * |
| " | $(ClCH_2CH_2O)_2P(O)OCH_2CH_2$ <br> \| <br> $(ClCH_2CH_2O)_2P(O)O$ <br> $CH_3OP(O)(OC_6H_5)_2$ | | 0.5% $Na_2CO_3$ | 135–190° | $ClCH_2CH_2Cl$ | ** |
| $CH_2=CHP(OCH_2CH_2Cl)_2$ <br> O= | " | 2 | 0.5% $Na_2CO_3$ | 130–190° | mostly $CH_3Cl$ | $CH_2=CH$ <br> \| <br> $(C_6H_5O)(CH_3O)P(O)CH_2CH_2OP(O)$ —O— |
| " | $(C_3H_7O)_2P(O)C_3H_7$ | 2 | 1% $Li_2CO_3$ | 200–210° | $C_3H_7Cl$ & $ClCH_2CH_2Cl$ | $(C_6H_5O)(CH_3O)P(O)OCH_2CH_2$ <br> $CH_2=CH$ <br> \| <br> $(C_3H_7)(C_3H_7)P(O)OCH_2CH_2OP(O)$ —O— |
| $CH_2=CHP(OCH_2CH_2Br)_2$ <br> O= | $(CH_3O)_2P(O)C_{18}H_{37}$ | 2 | 0.5% $Na_2CO_3$ | 130–190° | mostly $CH_3Br$ | $(C_3H_7)(C_3H_7)P(O)OCH_2CH_2$ <br> $CH_2=CH$ <br> \| <br> $(CH_3O)(C_{18}H_{37})P(O)OCH_2CH_2OP(O)$ —O— |
| $CH_2=CHP(OCH_2CH_2Cl)_2$ <br> O= | $(CH_3O)_2P(O)C_6H_5$ | 2 | 0.5% $Na_2CH_3$ | 130–190° | mostly $CH_3Cl$ | $(CH_3O)(C_{18}H_{37})P(O)OCH_2CH_2$ <br> $CH_2=CH$ <br> \| <br> $(C_6H_5)(CH_3O)P(O)OCH_2OCH_2OP(O)$ —O— |
| | | | | | $CH_2=CHCH_2Cl$ | $(C_6H_5)(CO_3O)P(O)OCH_2CH_2$ |

-continued

| Vinylphosphonate | ROP(O)XY | Mole Ratio ROP(O)XY to Vinyl-phosphonate | Catalyst | Temperature (° C) | Main Volatile Product(s) | Predominant (average) Structure in Residual Product |
|---|---|---|---|---|---|---|
| " | (CH$_2$=CHCH$_2$O)$_3$PO | 1 | " | 180-195° | and some ClCH$_2$CH$_2$Cl | * |
| CH$_3$ O<br>  |  ||<br>CH$_2$=C—P(OC$_3$H$_6$Cl)$_2$<br>(where C$_3$H$_6$Cl is 2-chloro-n-propyl or β-chloroisopropyl | CH$_3$P(O)(OCH$_3$)$_2$ | 2 | 0.5% Na$_2$CO$_3$ | 200-210° | mostly CH$_3$Cl | [(CH$_3$O)(CH$_3$)P(O)OC$_2$H$_3$(CH$_3$)O]$_2$P(O)C(CH$_3$)=CH$_2$ |
| " | " | 1 | " | " | mostly CH$_3$Cl | * |

*oligomeric mixture not readily depicted by a formula

EXAMPLE X

This example illustrates the use of one of the novel copolycondensates of this invention in the preparation of a textile finish which, in this case, does not contain an optional comonomer.

Part A

A sample of cloth comprising a 65:35 polyethylene terephthalate:cotton blend weighing 2.6 oz./yd.² is padded through an aqueous bath consisting of 50.6 parts of water, 1 part of a 10% aqueous solution of octylphenoxypolyethyleneoxyethanol, 36.4 parts of an ethylene oxide neutralized copolycondensate of 3 moles of bis(2-chloroethyl) vinylphosphonate and 4 moles of dimethyl methylphosphonate, 2 parts of a 25%, aqueous emulsion of a polyethylene softener and 10 parts of a 5% aqueous solution of $K_2S_2O_8$ catalyst. The treated fabric is then dried and cured at 300° F. for 5 minutes. The add-on was found to be 20.3%. When evaluated for flame retardancy, the treated fabric is found to have an LOI of 27.85.

Part B

The above described formulation is also applied to a 3.5 oz./yd.² cotton flannel fabric thereby depositing a 19.9% add-on. The LOI of the thus treated fabric is found to be 28.32.

EXAMPLE XI

This example illustrates the use of one of the unneutralized copolycondensates of this invention in preparing flame retardant textile finishes.

Samples of a 3.8 oz./yd.² cotton flannel cloth are padded through baths consisting of 35 parts water, 1 part of 10% aqueous solution of octylphenoxypolyethyleneoxyethanol, 26 parts of an unneutralized copolycondensate of 3 moles of bis(2-chloroethyl)vinylphosphonate and 4 moles of dimethyl methylphosphonate, 28 parts of a 60% aqueous solution of N-methylolacrylamide and 10 parts of a 5% aqueous solution of $K_2S_2O_8$. The treated samples are dried and cured at 300° F for 5 minutes and then evaluated for durable flame retardant properties as shown in the following table. As a control for this experiment, there is used an ethylene oxide neutralized sample of the identical copolycondensate in a bathing bath containing all of the above described ingredients.

|  | Copolycondensate | |
| --- | --- | --- |
|  | Un-neutralized | Neutralized Control |
| Vertical char length before washing | 4.5 in. | 4.75 |
| Vertical char length after 10 detergent washes | 3.75 in. | 3.75 |
| LOI before washing | 34.22 | 32.23 |
| LOI after 10 detergent washes | 29.37 | 29.97 |

EXAMPLE XII

This example illustrates the use of one of the novel copolycondensates of this invention in preparing a flame retardant finish on a polyester:cotton fabric.

A sample of a 50:50 polyethylene terephthalate:cotton blend weighing 3.5 oz./yd.² is padded through a bath consisting of 42.5 parts water, 1 part of a 10% aqueous solution of octylphenoxypolyethyleneoxyethanol,, 30 parts of a copolycondensate of 6 moles of bis(2-chloroethyl) vinylphosphonate and 7 moles of dimethyl methylphosphonate which has been neutralized with ethylene oxide, 6.3 parts of a 60% aqueous solution of N-methylol acrylamide and 10 parts of a 5% aqueous solution of $K_2S_2O_8$ catalyst. The treated fabric is cured 5 minutes at 300° F. and is found to have a 22.9% add-on.

The thus treated fabric is found to have a durable flame retardant finish as evidenced by an LOI value of 28.86 before washing and 27.68 after 50 detergent washes.

EXAMPLE XIII

This example illustrates the excellent resistance to chlorine bleaching which is displayed by the textile finishes derived from the novel copolycondensates of this invention. This property is extremely significant and represents one of the outstanding advantages which the flame retardant finishes of this invention have over the flame retardant finishes of the prior art.

A sample of (7 moles of dimethyl methylphosphonate,) 3.8 oz./yd.² cotton flanel fabric is padded through a bath consisting of 47 parts of water, 1 part of a 10% aqueous solution of octylphenoxypolyethyleneoxyethanol, 20 parts of an ethylene oxide neutralized copolycondensate of 6 moles of bis(2-chloroethyl) vinylphosphonate and 7 moles of dimethyl methylphosphonate, 22 parts of a 60% aqueous solution of N-methylolacrylamide and 10 parts of a 5% aqueous solution of $K_2S_2O_8$ and is subsequently cured for 5 minutes at 300° F. The treated fabric is then evaluated for its resistance to chlorine bleaching before and after 10 detergent washes. Thus, in each detergent washing cycle, there is introduced 1 cup of "Chlorox" bleach containing 5.25% available chlorine. The results of this evaluation are shown in the following table:

| | |
| --- | --- |
| Vertical char length before washing | 3.0 inches |
| Vertical char length after 10 detergent washes containing chlorine bleach | 4.5 inches |

The above data reveal that the textile finish of this invention retains substantially all of its flame retardancy even after having been exposed to 10 wash cycles containing a chlorine bleach.

EXAMPLE XIV

This example illustrates the use of one of the novel copolycondensates of this invention in the preparation of a flame retardant unsaturated polyester resin.

Polyester laminates are prepared by adding 5 parts, respectively, of each of the flame retardants listed in the following table, to 100 parts of a commercial polyester resin which is sold as "Hetron 24370" by the Hooker Chemical Co. and which comprises the styrenated polyesterification product of chlorendic anhydride, maleic anhydride and a glycol. As a curing catalyst, 2 parts of methyl ethyl ketone peroxide and 0.33 parts of cobalt naphthenate (6% solution) are added and the resulting compositions are each fabricated into a 5-ply glass laminate containing 35% of glass cloth. These laminates are allowed to cure at room temperature until a constant Barcol hardness is obtained, whereupon they are subjected to a stringent test for flammability. This test measures the total burning time of a vertical sample when it is ignited at its bottom with a burner in the timed sequence specified by the HLT-15 test. The latter test is described in detail in the Encyclopedia of Polymer Science, Vol. 7, page 6. The usual rating scale of 0 to 100 for this test is not employed, in this instance, since most of the compositions used in the experiment would rate 100 on this arbitrary scale and it would not, therefore, be possible to express the real differences in flame retardancy revealed by the observed burning times.

| Flame Retardant | Total Burning Time (sec.) |
|---|---|
| A 3:4 bis(2-chloroethyl) vinylphosphonate: dimethyl methylphosphonate copolycondensate | 23 |
| A 6:7 bis(2-chloroethyl) vinylphosphonate: dimethyl methylphosphonate copolycondensate | 32 |
| A homopolycondensation product of bis(2-chloroethyl) vinylphosphonate as described in Example VII | 73-80 |
| Tris(2,3-dibromopropyl) phosphate | 209 |
| Triethyl phosphate | 387 |

The above data clearly reveal the superior results obtained by the use of the copolycondensates of this invention in the preparation of flame retarded unsaturated polyester resins.

EXAMPLE XV

This example illustrates the use of one of the novel copolycondensates of this invention in preparing a flame retardant thermoset epoxy resin.

A cured thermoset epoxy resin is prepared by admixing the following ingredients:

| | Parts By Weight |
|---|---|
| Diglycidyl ether of bisphenol A sold as "Epon 828" by the Shell Chemical Co. | 10 |
| Copolycondensation product of 6 moles of bis(2-chloroethyl) vinylphosphonate and 7 moles of dimethyl methylphosphonate which has been neutralized by means of the procedure described in Part B of Example I | 10 |
| Triethylene tetramine (catalyst) | 6 |

The liquid mixture sets to a hard solid within 24 hours and is post-cured by heating for 24 hours in the oven at 100° C. The resultant product is found to be a solid polymer which is found to be completely non-burning under the conditions of ASTM D-635-56-T whereby a horizontal bar of the resin is subjected to a Bunsen burner flame.

The structure of this polymer is investigated by curing a thin film on a sodium chloride disc and thereafter observing the infrared spectrum of the resulting film. By this means, the double bond of the vinylphosphonate group is shown to have been consumed, presumably by the addition of —NH groups, since its characteristic absorption band at 1,620 cm$^{-1}$ has disappeared on curing.

EXAMPLE XVI

This example illustrates the use of one of the novel copolycondensates of this invention in preparing flame retardant polyethylene terephthalate fibers.

Into a melt containing 100 parts, by weight, of poly(ethylene terephthalate) which is at a temperature of 290° C., there is admixed 7.5 parts of the copolycondensation product of 3 moles of bis(2-chloroethyl) vinylphosphonate and 4 moles of dimethyl methylphosphonate which is prepared by means of a procedure comparable to that described in Example I. A monofilament is extruded from the resultant melt and is found to have a limiting oxygen index of 25.9 as compared to a limiting oxygen index of 20.8 for the fiber prepared from a melt of the unmodified polymer.

EXAMPLE XVII

This example illustrates the use of one of the novel copolycondensates of this invention as an intermediate for reaction with bromine which yields a brominated addition product useful as a flame retardant additive.

To 147.7 gms. of the copolycondensation product of 6 moles of bis(2-chloroethyl) vinylphosphonate and 7 moles of dimethyl methylphosphonate whose preparation is described in Example I there is added 60 gms. of bromine while maintaining the temperature at 30°-50° C. by the use of a cooling bath. The resulting addition product is found to impart self-extinguishing properties to cellulose acetate at a concentration of 20 parts per hundred of the resin.

Variations may be made in proportions, procedures and materials without departing from the scope of this invention as defined in the following claims.

What is claimed is:

1. A flame retardant polymeric resin composition containing at least one copolycondensed vinylphosphonate said copolycondensed vinylphosphonate comprising the product resulting from the reaction in stoichiometric ratio of from about 1:10 to 10:1 between a bis-(2-haloalkyl) vinylphosphonate and at least one pentavalent phosphorus ester of the structure ROP(=O)XY where R is selected from the class consisting of $C_1$-$C_{20}$ alkyl, $C_2$ - $C_{20}$ alkenyl, and $C_1$ - $C_{20}$ haloalkyl groups and X and Y are groups selected from the class consisting of RO -, $C_1$-$C_{20}$ alkyl, $C_2$-$C_{20}$ alkenyl, phenyl, phenoxy, amino, $C_1$-$C_{20}$ alkyl substituted amino, phenyl substituted amino, $C_2$-$C_{20}$ alkylene bonded to the same or to another ROP(=O) moiety and $C_2$-$C_{20}$ alkylenoxy and $C_2$-$C_{20}$ alkylenedioxy bonded to the same or to another ROP(=O) moiety, wherein said reaction is carried out at an elevated temperature for a period of time which is sufficient to evolve R-halide as a by-product and to form a P(O) — O— alkylene-O-P(O) linkage with the proviso that said product is not the homopolycondensed product of said bis-(2-haloalkyl) vinyl phosphonate.

2. The resin composition of claim 1, wherein moieties of an epoxy resin are also present.

3. The resin composition of claim 1, wherein moieties of a poly(ethylene terephthalate) are also present.

4. The resin composition of claim 1, wherein said copolycondensed vinylphosphonate comprises the reaction product of bis(2-chloroethyl) vinylphosphonate and dimethyl methylphosphonate.

5. The resin composition of claim 1, wherein moieties of an unsaturated polyester are also present.

6. The resin composition of claim 1, wherein said copolycondensed vinylphosphonate has been substantially neutralized with a neutralizing amount of an alkylating reagent.

7. The resin composition of claim 5, wherein said copolycondensed vinylphosphonate has been substantially neutralized by being reacted with a neutralizing amount of a reagent selected from the group consisting of alkanols, trialkylorthoformates and epoxide reagents.

8. The resin composition of claim 7, wherein said epoxide reagent is selected from the group consisting of ethylene oxide, propylene oxide, epichlorohydrin and the diglycidyl ether of isopropylidenediphenol.

9. The resin composition of claim 1, wherein said copolycondensed vinylphosphonate comprises the reaction product of bis(2-chloroethyl) vinylphosphonate and tris(2-chloroethyl) phosphate.

10. The resin composition of claim 1, wherein said copolycondensed vinylphosphonate comprises the reaction product of bis(2-chloroethyl) vinylphosphonate and trimethyl phosphate.

11. The resin composition of claim 3, wherein said copolycondensed vinylphosphonate comprises the reaction product of bis(2-chloroethyl) vinylphosphonate and dimethyl methylphosphonate.

* * * * *